United States Patent [19]

Smith et al.

[11] Patent Number: 5,433,954
[45] Date of Patent: * Jul. 18, 1995

[54] METHOD AND COMPOSITION FOR TREATING PSORIASIS, SEBORRHEIC DERMATITIS AND ECZEMA

[76] Inventors: Steven A. Smith; Lorraine J. Smith, both of 3010 S. Harvard Ste. 235, Tulsa, Okla. 74114

[ * ] Notice: The portion of the term of this patent subsequent to Dec. 15, 2009 has been disclaimed.

[21] Appl. No.: 985,610

[22] Filed: Dec. 3, 1992

Related U.S. Application Data

[63] Continuation-in-part of Ser. No. 518,170, May 1, 1990, Pat. No. 5,171,581.

[51] Int. Cl.⁶ ..................... A61K 33/24; A61K 31/28
[52] U.S. Cl. .................... 424/646; 424/617; 424/404; 424/723; 514/192; 514/250; 514/501; 514/863; 420/441; 423/493
[58] Field of Search ............ 424/617, 646, 404, 723; 514/501, 863, 192, 250; 420/441; 423/493

[56] References Cited

PUBLICATIONS

4, Cylopaedia & Medical Bulletin, pp. 348–355, "On the Uses of Nickel Sulfate in Medicine", by Louis Kolipinski, M.D. (1911).

The Merck Index, Windholz et al. editor, 10th Edition, Merck & Co., Rahway, N.J., 1983 pp. 932.

Weingartner et al., "Composition of the First . . . in Conc. Aqueous $NiCl_2$ and $NiBr_2$ Solutions", J. Chem. Soc., Faraday Trans., 1 75(12), 2700–11, 1978.

Sjovall, et al., "Oral Hyposensitization in Nickel Allergy", J. Amer. Acad. Dermatitis, V. 17, No. 5, Part 1, Nov. 1987.

Gawkrodger, et al., "Nickel Dermatitis: The Reaction to Oral Nickel Challenge;" Brit. J. Dermat., 115, pp. 33–38 (1986).

DaCosta, J. M., "Observations on the Salts of Nickel, Especially the Bromide of Nickel", The Medical News, vol. XLIII, No. 13 (1883).

Jordan, W., "Nickel Feeding in Nickel-Sensitive Patients with Hand Eczema", J. Am. Acad. Dermatol., vol. 1, No. 6 (1979).

*Primary Examiner*—Gary E. Hollinden
*Assistant Examiner*—B. Bembenick
*Attorney, Agent, or Firm*—Steinberg, Raskin & Davidson

[57] ABSTRACT

Psoriasis, seborrheic dermatitis and eczema are treated by oral administration of inorganic nickel compound(s), with or without inorganic bromide(s). In an especially preferred embodiment, the nickel compound used to treat these diseases is $NiBr_2$.

23 Claims, No Drawings

METHOD AND COMPOSITION FOR TREATING PSORIASIS, SEBORRHEIC DERMATITIS AND ECZEMA

This application is a continuation-in-part application of U.S. application Ser. No. 07/518,170, filed May 1, 1990 (now U.S. Pat. No. 5,171,581).

BACKGROUND OF THE INVENTION

Psoriasis is a chronic skin disorder that is proliferative in nature and widespread throughout the world, afflicting millions of humans and even domesticated animals having similar proliferative integument problems. The skin disorder is characterized by recurrent, elevated red lesions, plaques or rarely pustules on the skin. These plaques are the results of an excessively rapid growth and shedding of epidermal (skin) cells.

No one knows what causes this abnormal cell proliferation. Its severity and course vary greatly from case to case, and also in the individual afflicted with the disease. Recurrences are almost the rule with intervals varying from one month to many years. One person may go through life with a single patch on the elbow, knee or scalp, while another will have repeated attacks of a generalized eruption or widespread chronic lesions lasting for years without remission. As discouraging as it may be, medical science and literature are replete with indications that patients exhibiting such lesions are destined for life to be "psoriatic." With all of the advances in medical science, no one knows what causes this abnormal cell proliferation. With some of it, it is felt that some type of biochemical stimulus triggers this abnormal cell growth. It is still unknown whether the origin of this biochemical malfunction resides in the skin, in the immune system, in the white blood cells, or is possibly psycho-neural. It is known that certain environmental factors can "trigger" the initial appearance or worsening of psoriasis. Conversely, the symptoms can spontaneously clear for reasons scientists do not understand. Treatment of the psoriasis is aimed at clearing the lesions for as long as possible. This is what is meant by the term "remission" or "clearance." In any event, medical science has fairly well agreed that psoriasis is an heritable disease in which the specific defect seems to be unknown.

For years there have been many attempts to treat the disease, and several topical and systemic treatments for psoriasis which inhibit cell division have been with limited success in clearing the skin for short periods of time. Yet, the reason why these treatments work is not yet clearly understood. Treatments which have been suggested in the art appear to be symptomatic and palliative. Lesions may disappear spontaneously or as a result of the therapy, but recurrences are likely. There is a tendency for each remedy gradually to lose its effectiveness or develop dangerous accumulative toxicity. Rarely, however, is the disease apparently cured, showing no evidence for years.

In the treatment of the disease, medical science has suggested low fat or low protein diets. Drugs such as systemic corticosteroids and ACTH are effective but limited to patients who are in great distress and do not respond to other measures. Such drugs may produce dangerous side effects; and in some instances, once the drugs are discontinued, the eruption may show a marked exacerbation. Folic acid antagonists have been found to have some beneficial treatment but are a dangerous form of therapy. Although other drugs have been suggested, for the most part the serious side effects associated therewith have not made them successful. Ionizing radiation therapy, e.g. grenz-ray treatment, has provided only temporary benefit, but the danger(s) of addiction to such radiation producing radiodermatitis and subsequent carcinoma is not worth continued treatment. Corticosteroid ointment in combination with polyethylene film has had some success, but systemic effects may be caused by extensive use. Ointments have been found to be more beneficial than lotions. A typical ointment may contain anthralin or tar. Hydrophilic ointment containing salicylic acid and sulfur is also found to be beneficial, especially for scalp treatment. Here again, the side effects and the absorption within the human system of these chemicals must be guarded. Other treatments including sunlight baths or ultraviolet (UV) baths with the lesions painted with a solution of coal tar, anthralin or psoralens have been found to be helpful.

Ongoing studies in the art concern the use of vitamin $D_3$ (1,25-dihydroxivitamin $D_3$). Etretin and Etretinate are new generation retinoids presently being studies for treating psoriasis, but again, the side effects must be carefully monitored.

Other ongoing studies include the use of the drug cyclosporine, RS 53179 (a non-steroidal, anti-inflammatory drug), fish oil, hypothermia, and anti-yeast agents.

One method for alleviating psoriasis is taught in U.S. Pat. No. 4,181,725 which teaches a pharmaceutical compound which contains as its active components at least one compound selected from the group consisting of parabromophenacyl bromide, alpha tocopherol, mepacrine, chloroquine, hydroxychloroquine, dibucaine, tetracaine, lidocaine, butacaine, procaine, ethylene diamine tetra, acetic acid, and ethylene glycol bis ($\beta$ amino ethyl ether) -N-N'tetracetic acid within a suitable carrier.

Seborrheic dermatitis (seborrhea) in the least severe form, but most common, is simple dandruff. It can become more severe and form scaly, red patches on the face, ears, chest, and other widespread areas. It often coexists with psoriasis, and many subjects have overlapping features termed "seborrhiasis." Therefore, a continuum may exist whereby these are on the same disease spectrum. Treatments are similar to those currently used for psoriasis, although lower dosages are usually sufficient to control seborrheic dermatitis.

Eczema (including but not limited to atopic, nummular and hand types) often has similar overlapping features with psoriasis. See, e.g., H. Roenigk, Jr. et al., "Psoriasis", ©1991, Marcel Dekker, Inc., Chapter 2. For instance, it is often difficult to distinguish based on clinical appearance. They can coexist, or the disease can begin as eczema and over time turn to psoriasis. Again, treatments are similar with corticosteroids and tar preparations commonly employed for both of these conditions.

Similar conditions to both seborrheic dermatitis and eczema also occur in various domestic animals (mange, etc.). The current invention is felt to encompass all similarly involved species.

Seborrheic dermatitis and eczema have several other features in common with psoriasis. They are very common in the general population. They have no known cause, although many theories are advanced. They have no known cure, although many similar temporary remedies are known. All of these conditions are known to worsen with stress. Finally, there seems to be a hereditary basis or tendency for development of each of these skin disease, although this is not a strict finding.

SUMMARY OF THE INVENTION

The present invention is directed to and encompasses as its object to provide methods and composition for the topical, oral, or intravenous treatment of psoriasis, seborrheic dermatitis and eczema (including but not restricted to atopic, nummular and hand types). The treatment of other diseases such as primary irritant contact dermatitis, allergic contact dermatitis, lamellar ichthyosis, epidermolytic hyperkeratosis, and certain forms of dermatitis and mange in domesticated animals and psoriatic arthritis are also intended to be encompassed by the appended claims.

It is believed that there is/are specific defective enzyme(s) in humans that is/are genetically predisposed to psoriasis, seborrheic dermatitis and eczema. Certain exacerbating factors (lithium, stress, etc.) interfere with the function of such enzyme(s). It is believed this leads to a buildup of a metabolically active "psoriasis molecule(s)" which in turn either directly or indirectly triggers inflammation in the skin and/or joints. It is believed that the hematopoietic system (especially leukocytes) is the most likely source and most prolific producer of the "psoriasis molecules." A hepatic enzyme(s) probably compounds the problem by failing to catabolize and/or excrete this molecule(s). A defective kidney enzyme(s) may also play a role.

Specifically, this invention proposes and has for its single compound and/or separately and/or oral processes which favorably affect the aforementioned enzyme(s) in people predisposed to psoriasis, seborrheic dermatitis and eczema. Pharmaceutically acceptable inorganic nickel compound(s) with or without accompanying inorganic bromide(s) are administered to diseased subjects over time with alleviation of the signs and symptoms of the disease(s).

The exact mechanism of this beneficial action on these diseases is not well understood at this time. It is felt, however, that nickel-dependent metalloenzymes are partially defective in diseased subjects, thus requiring additional nickel for greater efficiency of action and consequent improvement in the diseased condition. This hypothesis is not meant to limit the scope of the claims in any manner whatsoever.

More particularly, the present invention is related to a method of treating human beings for psoriasis, seborrheic dermatitis and eczema comprising the step of orally administering an effective amount of a disease-inhibiting formulation containing a non-toxic, pharmaceutically acceptable nickel (Ni) salt(s) in a human patient, and dosing the patient such that said formulation provides an amount of nickel from about 2 to about 300 mcg/kg (micrograms per kilogram) of patient weight/day is administered. In a preferred embodiment, the nickel salt is $NiBr_2$, $NiSO_4$, $NiCl_2$, mixtures of any of the foregoing, etc. In an especially preferred embodiment, the nickel salt is nickel bromide ($NiBr_2$).

The present invention is also related to a composition for treating psoriasis, seborrheic dermatitis and eczema in human beings comprising nickel (Ni) in an amount from about 2 to about 300 mcg/kg of patient weight/day, the dosage of Ni being derived from a non-toxic pharmaceutically acceptable Ni salt(s). The composition may be in any pharmaceutically acceptable form for oral administration, including liquid, capsule, and tablet form.

In a preferred embodiment, the dosage of said Ni is present in an amount for treatment within the range of from about 5 to about 150 mcg/kg of patient weight/day. In other preferred embodiments, nickel is orally administered in an amount from about 5 to about 50 mcg/kg of patient weight/day.

DETAILED DESCRIPTION AND EXAMPLES

A human tissue cell membrane, such as a liver cell or hepatocyte, contains certain sub-cellular organelles which are specialized parts of a protozoan or tissue cell. These subcellular units include mitochondria, the Golgi apparatus, cell center and centrioles, granular and agranular endoplasmic reticulum, vacuoles, microsomes, lysosomes, plasma membrane, and certain fibrils, as well as plastids of plant cells. Leukocytes and perhaps other rapidly dividing cells are believed to be the primary site of production of the "psoriasis molecule" (P.M.). Hence it is an object of this invention to biochemically and/or genetically change or reduce the effect of this hideous disease by treating the affected sub-cellular organelles with compounds of nickel and bromide. The key to the invention is to effect transport of the element nickel (Ni) into the cell and sub-cells, such as the mitochondria or Golgi wherein the needful metalloenzymes can catabolize P.M. into a less toxic and/or easier excreted molecule. It is believed the rejection of nickel from the cell prevents a biochemical change in the P.M. to a less toxic form. It is believed that the use of Br with Ni is an effective carrier to overcome this rejection. The P.M. may then be changed to a less toxic catabolic product by treatment of a nickel dependent metalloenzyme located in the sub-cellular organelles. The nickel (Ni)/bromide (Br) of the invention may become a "catalytic lever" or "switch" to activate the metalloenzyme to its maximum function. This hypothesis is provided for discussion purposes only, and is not meant to limit the appended claims in any manner whatsoever.

Since the exact etiologies of these diseases are not known, one cannot pinpoint the exact beneficial mechanism of action of this invention. However, the inventors believe that there exists an inherited enzymatic defect in diseased individuals that leads to a buildup of a metabolic substrate that triggers a cascade of immunologic mechanisms that causes disease manifestation.

It is believed that this defective enzyme is a nickel-dependent metalloenzyme, and that supplying it with additional nickel can assist in the general efficiency of this enzyme's function. Thereby, the above-mentioned metabolic substrate can be more easily converted into a less toxic and/or more easily excretable metabolic product.

The bromide(s) role is not fully understood at this time, but it seems to be one of facilitator, either through physiological assistance in nickel transport, absorption, or some more direct enzymatic action. Bromide is not felt to be an absolute requirement for utility of this invention but may be required for greater safety and greater effectiveness.

One form of the invention is directed to the topical or oral use of nickel dibromide ($NiBr_2$) or $NiBr_2$ hydrate in adult dosages within the range of 0.037 mg to 370 mg $NiBr_2$ per dose. As such, this is equivalent to the use of 0.01 mg to 100 mg of Ni per dose. The dosages can be mixed in sucrose or lactose or other appropriate form and can be contained within a gelatin capsule or other appropriate oral vehicle. With children, the pediatric dosage is 0.001 mg to 10 mg of NiBr$_2$ per kg per dose within purified or distilled water plus any form of pleasant-tasting flavoring (elixir). The dosages can be available for a variety of situations, including from once a week or once a month to once or twice daily dosages. In some instances, once a day for 5 to 15 days per month for up to 6 months may be effective. It may be desirable or necessary to provide bromide preloading and/or post loading wherein 5 to 500 mg of bromide would be given orally (p.o.) in capsule or elixir in a form such as sodium bromide, potassium bromide, or ammonium bromide or combinations of these which would be given in dosages once daily from 5 to 15 days prior to or after the dosing of NiBr$_2$. In other instances, bromide formulations may be given simultaneously with the NiBr$_2$.

Another process for treatment would include first obtaining a nickel patch test of a patient to determine if there is any contact allergy. To determine effectiveness, pre-treatment color photographs of the psoriasis lesions would be obtained prior to starting. Also, pre-treatment color photographs of the psoriasis lesions would be obtained prior to starting. Also, pre-treatment serum tests for nickel, bromide, zinc and copper, a complete blood count (CBC), and a sequential multichannel autoanalyzer count (SMAC) would be accomplished. A 90 kg man would ingest 2 mg of nickel as nickel sulfate (NiSO$_4$) and 20 mg of bromide (Br as sodium bromide (NaBr) per day. These are mixed together in 15 cc of distilled or purified water and taken once daily p.o. on an empty stomach. This process would be repeated for 21 days. Subsequently, a nickel patch test would be taken at a three-week anniversary, photographs taken weekly after starting the process, and post-treatment serum tests as identified in the pre-treatment tests are repeated.

References and studies indicate that the use of NaBr is within well-recognized safe limits. For example, if 20 mg of bromide by way of NaBr were given orally once a day for 21 days, it would be equivalent to 420 mg given assuming 100 percent (100% absorption and an acceptable daily intake (A.D.I.) were 0.4 mg/kg/day. Thus, for a 90 kg adult male, 20 mg of bromide per day is well under the A.D.I. or 35 mg per day. Reference is made to Van Leeuwen, F. X. et al., The Toxicology of Bromide; *CRC Critical Reviews in Toxicology*, 18:189–213; (1987). This reference indicates that the dietary intake in the United Kingdom and in the Netherlands is within the range of 2–17 mg per day. There are apparently no studies on the carcinogenicity. Bromide has been given for 140 years without any carcinogenic effect being reported. See Livingston S. et al.; Bromides in the Treatment of Epilepsy in Children; *American Journal of Diseases of Children*; 86:717–720; (1953). Likewise, the literature indicates that the quantitative exposure giving a 90 kg adult male 2 mg nickel (Ni) by way of NiSO$_4$·6H$_2$O orally and daily for 21 days will equal 42 mg given. This daily dose is approximately two times higher than that recommended for contaminated IV fluids per day and twenty percent (20%) of dose causing increased coronary artery resistance in single IV dose in dogs. Assume five percent (5%) of the nickel absorbed would equate to 2.1 mg. Assuming thirty percent (30%) of that which is absorbed is deposited in tissues for a mean retention time of 200 days, 30 micrograms (0.3×100) retained each day for the 21 days would equate to a total of 630 micrograms retained. If the normal body burden of Ni equals 7 micrograms per kg, therefore, approximately 21 days will be required to double body burden of Ni for a 90 kg adult. Reference is made to Sunderman, F. W., Sr.; Potential Toxicity from Nickel Contamination of IV Fluids. Soluble nickel salts such as nickel chloride, nickel sulfate, and nickel ammoniumsulfate, have not been shown to be carcinogenic; Sunderman, F. W. Sr.; A Review of the Metabolism and Toxicology of Nickel; *Annals of Clinical and Laboratory Science*; 7:377–398; (1977).

Hence, based on the literature and the studies, it would appear that the use of nickel sulfate and sodium bromide can be effectively employed. The bromide may be absorbed topically from bath solutions or other formulations in creams, ointments, or lotions.

An exemplary test includes two psoriatic patients with active skin disease and a healthy control. The test subjects will be immersed in water high in bromide content. The water of the Dead Sea is found to be of that quality. The subject would be immersed, neck down, for 30 minutes every hour for two four-hour sessions daily for a total of ten days. All activities, including bathing, will be done in sun-shaded facilities, and no suntanning will be permitted. Prior to the study, nickel patch testing as above-described is done on all the subjects, and no medications of any type (systemic of topical) will be taken for at least six weeks prior to the study, during the study, and for six weeks after the study. Only bland emollients will be permitted. Nickel sulfate containing 2.5 mg of nickel is administered orally twice daily during the ten-day study at the beginning of each four-hour bathing session. The aforesaid serum and urine level tests for bromide and nickel will be obtained from all test subjects prior to the onset of each treatment day and at the end of the treatment period with similar levels being tested at the end of each week after therapy. The CBC, SMAC, serum zinc, and serum copper levels will be studied at the beginning and the end of the treatment period and at the end of the study, followed by a nickel patch test.

DETAILED DESCRIPTION OF PREFERRED EMBODIMENTS

The following examples illustrate various aspects of the present invention. They are not to be construed to limit the claims in any manner whatsoever.

EXAMPLE 1

A preliminary study was conducted in conjunction with a 39 year old white male who had over a 15-year history of difficulty controlling the plaque-type of psoriasis vulgaris. The patient had been treated for approximately five years previously with limited success, with maximum b range ultraviolet rays (UVB), along with topically applied tar, corticosteroids, and 5-fluorouracil. The history of the patient showed active flaring of the plaque type of psoriasis over 20 to 30% of the body surface area which were scaly and thickened. No pustules nor inverse patterns were noted. There was minimal involvement of the disease on the face, and the palms of the hands were spared.

Prior to treatment, the following evaluations were conducted: nickel patch testing, exercise tolerance testing, serum nickel, bromide, zinc, copper, SMAC, blood CBC drawn, and preliminary photographs of the affected areas were taken.

The solution itself was obtained by mixing together nickel sulfate (NiSO$_4$)·6H$_2$O and sodium bromide.

Nickel dibromide (NiBr$_2$) resulted in a 5 mg/50 mg ratio of Ni to Br. These were mixed together in purified water to a concentration of 2 mg of Ni and 20 mg of Br per 15 cc of solution. These compounds mixed easily into a colorless solution and were placed in a standard, round, glass pharmacy jar. The compound minerals themselves were ASC grade and purchased from New York City Chemical Corporation. The study comprised the patients' ingestion of very small amounts of the subject solution in order to effect ingestion of 2 mg of nickel and 20 mg of bromide once daily for 21 days. Every seven days standard photos were taken; and on day 21, laboratory tests of serum, nickel, bromide, zinc, copper, SMAC, and blood CBC were conducted. The ingestion by the patient was to be conducted on an empty stomach. Following the treatment, a nickel patch test was conducted along with standard photographs at one-week, three-week, and five-week intervals, with tests for serum nickel and bromide at three weeks post treatment.

During the three-week course of therapy, the following results were noted:

1. No new psoriatic lesions (plaques) were noted at one week and two weeks into therapy. There was a very rare new papule noted at three weeks into therapy. This is a positive result, especially when considered in the setting of rapidly flaring disease prior to the initiation of this treatment and since this patient was in the midst of some severe domestic stresses during the treatment period. Stress has been considered a factor in triggering psoriasis lesions.
2. The existing lesions became less scaly and less reddened and thinner during the entire treatment course. The periphery (circumference) enlarged minimally, and small areas of more normal appearing skin appeared in their centers during treatment.
3. One area on the central chest showed more pronounced clearing than any of the rest of the lesions. There was approximately 50% complete clearing in this area.

At three weeks post-treatment, i.e. the patient was completely off treatment for three weeks, there was noticeable worsening on all the above parameters (new lesions forming, existing lesions turning more bright red in color and producing more bothersome scaly buildup, and all lesions thickening notably).

The above findings are felt to reflect favorable effects of the study medication on the test patient's skin.

MODIFICATIONS

Although certain specific forms of nickel and bromide compounds are set forth herein, other pharmaceutically acceptable compounds are inclusive of the invention, e.g. nickel sulfate (NiSO$_4$), nickel chloride (NiCl$_2$) sodium bromide (NaBr), potassium bromide (KBr) and ammonium bromide (NH$_4$Br).

In many instances pre, during, and/or post treatment will include topical and/or systemic (oral) or intravenous use of anti-bacterial compounds, e.g. penicillin, and anti-fungal agents, e.g. Ketoconazole.

EXAMPLE 2

In vivo studies have been made to investigate the effects of a nickel bromide oral solution therapy for an individual with psoriasis. Details of these studies and their positive results are as follows.

There were three phases to a first clinical study of an adult 41 year old male including Pre-Treatment, Treatment, and Post-Treatment. The test subject was selected due to longstanding treatment-resistant plaque-type psoriasis vulgaris. He was also very ready to try new and innovative therapies. Informed consent was obtained.

During the Pre-Treatment Phase various baseline laboratory studies were obtained including skin and throat cultures and routine hematology and blood chemistries. Blood levels of nickel, bromide, copper, and zinc were documented. Standard whole body and close-up clinical 'before' photographs were also obtained. A two week course of antibiotics Pen VK 500 mg qid, Rifampin 600 mg qd, and Nizoral 400 mg qd (antifungal) was given the patient. This permitted study of the effects of such antibiotics.

The Treatment Phase consisted of daily oral administration of nickel dibromide aqueous solution in dosages ranging from 2-50 micrograms (mcg) of Ni/kg of patient weight/day. Standard photographs, as well as blood testing similar to the Pre-Treatment regimen, were obtained. Standard clinical assessments were also documented at all phases.

Post-Treatment Phase included all of the above-mentioned blood tests and standard photographs as well as standard nickel cutaneous patch testing.

TEST ARTICLE AND VEHICLE

Chemical grade nickel di-bromide was obtained from New York City Chemical Company. This was carefully weighed on an analytical scale and was mixed with appropriate volumes of purified and distilled water. This was readily soluble and stored in a brown pharmacy bottle. All appropriate chemistry calculations were taken to assure accurate concentration and dosing.

STUDY COURSE

Daily dosing was accomplished by the test subject measuring a pre-defined amount of test medication into a graduated dose cup. Daily dosing was taken on an empty and fasted stomach.

RESULTS OF CLINICAL OBSERVATIONS

During the first 10 weeks of therapy, the patient had approximately 95% clearing of total body psoriasis lesions based on clinical examinations and serial clinical photographs. Nickel di-bromide aqueous solution was given orally at very low doses. Notable improvement of toenail psoriasis was documented. The average nickel dose during the first 10 weeks of therapy was 12.5 mcg/kg/day which was equivalent to 50 mcg/kg/day of NiBr$_2$. Clinical symptoms of itching and burning of the skin were improved within one week of starting therapy. Notable improvements of skin lesions were documented and photographed within two weeks of starting therapy. These improvements consisted of thinning psoriasis plaques as well as loss of scale and fading of the degree of erythema (inflammatory redness of the skin).

In the following seven weeks the average nickel dosage was reduced to 4.6 mcg/kg/day (equivalent to 18.4 mcg/kg/day of NiBr$_2$). There was a slow reappearance of the symptoms and a possible worsening of some of the existing psoriasis lesions.

Overall, patient acceptance of the medication was high, and at the end of the therapy the patient wished to continue taking it even though it had to be discontinued due to the study design.

EXAMPLE 3

A subsequent study was conducted with a variety of patients with certain selection criteria as follows: (1) They had to be in good health and on no medications; (2) They had to be between the ages of 18–58 years old; (3) Women needed to have no child-bearing capacity; (4) Patients needed to weigh between 40–100 kg; (5) Patients needed to have no known industrial exposure to nickel or pharmaceutical/other exposure to bromides; (6) They needed to have reasonably normal renal and hepatic function on routine blood testing; and (7) They needed to discontinue all preexisting medications for at least two weeks prior to the study. Subjects were allowed to maintain bland emollients during the study, however, no prescription or even over-the-counter medications were allowed other than the test article.

There were three phases to this study including Pre-Treatment, Treatment, and Post-Treatment.

During the Pre-Treatment Phase (week 0), various baseline tests were conducted. These consisted of routine hematology and serum chemistry as well as blood testing for nickel, bromide, zinc, and copper. A routine patch test for nickel was also conducted prior to the study and then repeated at the end of therapy (See Post-Treatment phase below). Clinical history and examinations were obtained as well. All patients had routine stable and/or flaring plaque-type psoriasis vulgaris. All patients had classic cases with no question regarding the diagnosis. All patients gave their voluntary consent to participate in this study. Standard whole body and close-up clinical photographs of selected regional areas were also obtained.

The treatment phase consisted of daily oral administration of nickel di-bromide aqueous solution. The dose for all patients was standardized to 10 mcg/kg/day of nickel component (equivalent to 40 mcg/kg/day of $NiBr_2$). All of the Pre-Treatment Phase testing was again accomplished at four weeks and eight weeks of treatment. Standard clinical assessments and photographs were also documented at all phases. Treatment was terminated at 8 weeks.

Post-Treatment Phase consisted of four weeks of follow up immediately following the Treatment Phase. All the blood testing done during the Pre-Treatment Phase was again accomplished at the end of the Post-Treatment Phase (12 weeks). This included standard nickel patch testing as well as clinical assessments and standard clinical photographs.

TEST ARTICLE AND VEHICLE

Nickel di-bromide powder was obtained from Alfa Inorganics. This was rated as anhydrous and 99% purity. Appropriate amounts of this powder were weighed on an analytical scale and carefully mixed with appropriate volumes of purified and distilled water. This was readily soluble and stored in brown pharmacy bottles. All appropriate chemistry calculations were taken to assure accurate concentration and dosing.

Daily patient dosing was accomplished by the test subject measuring a predefined amount of the test vehicle into a graduated dose cup. This amount was determined by the patient's weight and the Study Design. Daily dosing was taken on an empty and fasted stomach (at least 8 hours after having eaten and at least one hour prior to eating).

RESULTS OF CLINICAL OBSERVATIONS

Five patients were initiated on the study. Four of the patients had no side effects or adverse reactions to the test article/medication (daily oral aqueous solution of nickel di-bromide). One patient had gastrointestinal distress which soon stopped after the medication was discontinued and she was removed from the study. The remaining four patients completed the study without any side effects. Of these, two were men and two were women. The two men both had marked improvements of all skin disease, substantially 95% clearing. Skin parameters followed included erythema, elevation, and scale present on existing plaques.

One of the two women patients improved moderately on treatment with about 35% clearing of the psoriasis. Substantially all of the thin plaques cleared. The thicker sacral and leg plaques did not clear, but their appearance changed during the therapy. The other female patient showed no noticeable improvement. The clinical significance of this is not known. Skin improvements on the three patients occurred between 4–8 weeks during the treatment phase. The patients who noted improvement during the treatment phase also continued to improve during four weeks of post-treatment follow up. The compliance by the four patients was good. Patient acceptance of the medication was also quite good with each of the four patients requesting to stay on the medication. This was not allowed due to the nature of the study. It is believed that there was sufficient marked improvement in a sufficient number of people that indicates that the concepts of the invention as disclosed and claimed will provide some relief from psoriasis lesions.

EXAMPLE 4

A study was performed from 9/91 to 3/92 on one subject with seborrheic dermatitis. This condition had existed for several years and manifested as scaly, itchy scalp. Previous treatments included tar and other medicated shampoos which were required continually for control of this disease.

Once daily oral administration of $NiBr_2$ aqueous solution was given at a dosage of 56 mcg/kg/day (equivalent to 15 mcg/kg/day nickel component) for 19 weeks.

Pre-treatment, treatment and post-treatment evaluations were conducted including regular exams and appropriate laboratory testing (serum chemistry profile, complete blood count profile, serum nickel and bromide, and zinc and copper, and routine urinalysis). Nickel patch testing for cutaneous sensitivity was done at the pre and post-treatment intervals.

Results of this study showed no adverse reactions. All laboratory parameters remained within pre-treatment limits except serum nickel and bromide which elevated appropriately. Efficacy evaluations showed clearance of all signs and symptoms of seborrheic dermatitis after sixteen weeks of treatment. This favorable response persisted for nine months of post-treatment follow up, despite absence of therapy of any type during this interval. This type of remittive therapy is unique compared to existing accepted treatments.

The examples provided above are not meant to be exclusive. Many other variations of the present invention would be obvious to those skilled in the art, and are contemplated to be within the scope of the appended claims.

What is claimed is:

1. A method of treating seborrheic dermatitis in human patients, comprising orally administering an aqueous or saline solution comprising from about 2 to about 300 mcg/kg of patient weight of nickel (Ni) per day for a period of time sufficient to substantially alleviate or improve the symptoms of the condition, said Ni being derived from a non-toxic, pharmaceutically acceptable nickel salt.

2. The method of claim 1, wherein said formulation is in a dosage form selected from the group consisting of liquids, powders, capsules and tablets.

3. The method of claim 1 wherein said Ni is derived from $NiBr_2$.

4. The method of claim 1 wherein said formulation provides an amount of nickel from about 5 to about 150 mcg/kg of patient weight/day.

5. The method of claim 1 wherein said formulation provides an amount of nickel from about 5 to about 50 mcg/kg of patient weight/day.

6. The method of claim 1, wherein said formulation is administered as an aqueous or saline solution.

7. The method of claim 1, further comprising orally administering a further treatment for seborrheic dermatitis selected from the group consisting of anti-bacterial agents, anti-fungal agents, and a combination of the foregoing.

8. The method of claim 6, further comprising the step of adding an agent selected from the group consisting of a flavoring agent, a preservative, a non-toxic colorant, and a combination of the foregoing.

9. A unit dose of an oral pharmaceutical formulation for treating psoriasis, seborrheic dermatitis and eczema in human patients comprising nickel (Ni) in an amount from about 2 to about 300 mcg/kg of patient weight, the dosage of Ni being derived from a non-toxic pharmaceutically acceptable Ni salt(s) or Ni compound(s) selected from the group consisting of $NiBr_2$, $NiSO_4$, $NiCl_2$ and mixtures thereof, wherein when said nickel salt or compound is other than $NiBr_2$, the composition further includes a bromide salt selected from the group consisting of $NiBr_2$, NaBr, KBr, $NH_4Br$ and mixtures thereof such that the amount of bromine in said composition is proportional to the amount of nickel included in the composition calculated based on $NiBr_2$.

10. A unit dose of an oral pharmaceutical formulation for treating psoriasis, seborrheic dermatitis and eczema in human patients comprising nickel (Ni) in an amount from about 2 to about 300 mcg/kg of patient weight, the dosage of Ni being derived from $NiBr_2$.

11. The unit dose of claim 10, comprising nickel in an amount from about 5 to about 150 mcg/kg of patient weight.

12. The unit dose of claim 10, comprising nickel in an amount from about 5 to about 50 mcg/kg of patient weight.

13. The unit dose of claim 10, wherein said dosage form is a capsule or tablet.

14. The unit dose of claim 10, wherein said formulation is administered as an aqueous or saline solution.

15. The unit dose according to claim 14 which comprises by weight percent: 99.93 distilled water; 0.02% Ni; and 0.05% Br.

16. The unit dose of claim 9, further comprising an agent selected from the group consisting of a flavoring agent, a preservative, a non-toxic colorant, and a combination of the foregoing.

17. The unit dose of claim 10, further comprising an effective amount of a medicament selected from the group consisting of anti-bacterial agents, anti-fungal agents, and a combination of the foregoing.

18. The unit dose of claim 9 which is a capsule or tablet containing from about 80 mcg to about 30,000 mcg nickel.

19. A method of treating seborrheic dermatitis and/or eczema condition in human patients, comprising orally administering to an affected human patient a unit dose of nickel from about 2 to about 300 mcg/kg of patient weight/day over a period of time sufficient to substantially alleviate or improve the symptoms of the condition, said dose of nickel being derived from a nickel salt(s) selected from the group consisting of $NiBr_2$, $NiSO_4$, $NiCl_2$ and mixtures thereof, wherein when said nickel salt or compound is other than $NiBr_2$, the composition further includes a bromide salt selected from the group consisting of $NiBr_2$, NaBr, KBr, $NH_4Br$ and mixtures thereof such that the amount of bromine in said composition is proportional to the amount of nickel included in said unit dose, calculated based on $NiBr_2$.

20. The method of claim 19, further comprising dosing the affected human patient for a period of time up to about six months, until the condition is improved or alleviated.

21. A solid oral unit dosage form comprising a therapeutically active agent consisting of nickel in the form of nickel bromide, the nickel content of said formulation being from about 80 mcg to about 30,000 mcg.

22. The solid oral unit dosage form of claim 21 wherein said dosage form is selected from a tablet or capsule.

23. A unit dose of a medicament for treating psoriasis, seborrheic dermatitis and/or eczema in human patients comprising nickel in an amount from about 80 mcg to about 30,000 mcg, said nickel being derived from a nickel salt(s) selected from the group consisting of $NiBr_2$, $NiSO_4$, $NiCl_2$ and mixtures thereof, wherein when said nickel salt is other than $NiBr_2$, said unit dose further includes an effective amount of a bromide salt selected from the group consisting of $NiBr_2$, NaBr, KBr, $NH_4Br$ and mixtures thereof, to substantially alleviate or improve the symptoms of the condition.

* * * * *